United States Patent [19]

Masilamani et al.

[11] Patent Number: 5,171,891

[45] Date of Patent: Dec. 15, 1992

[54] OXIDATION OF ORGANIC COMPOUNDS HAVING ALLYLIC OR BENZYLIC CARBON ATOMS IN WATER

[75] Inventors: Divakaran Masilamani, Morristown; David M. Hindenlang, Randolph, both of N.J.

[73] Assignee: Allied-Signal Inc., Morristown, N.J.

[21] Appl. No.: 91,625

[22] Filed: Sep. 1, 1987

[51] Int. Cl.$^5$ .............................................. C07C 51/16
[52] U.S. Cl. ..................................... 562/411; 568/309; 568/426; 568/910
[58] Field of Search ................ 562/411; 568/309, 426, 568/910

[56] References Cited

U.S. PATENT DOCUMENTS 2,900,412  8/1959  Toland, Jr. .......................... 562/411
2,903,480  9/1959  Toland, Jr. .......................... 562/411

Primary Examiner—Arthur C. Prescott
Attorney, Agent, or Firm—R. C. Stewart, II; G. H. Fuchs; D. L. Webster

[57] ABSTRACT

The present invention is directed to a process of oxidizing organic compounds having allylic or benzylic carbon atoms. The process of this invention comprises reacting an organic compound having one or more allylic or benzylic carbon atoms with an effective amount of an effective oxidizing agent in water at a temperature equal to or greater than about 350° C. and at a pressure equal to or greater than about 175 atmospheres, wherein said agent is selected from the group consisting of elemental sulfur, an oxidized form of elemental sulfur and, an organic or inorganic compound capable of forming elemental sulfur or said oxidized forms in situ under process conditions.

24 Claims, No Drawings

OXIDATION OF ORGANIC COMPOUNDS HAVING ALLYLIC OR BENZYLIC CARBON ATOMS IN WATER

BACKGROUND OF THE INVENTION

This invention relates to the oxidation of organic compounds having allylic or benzylic carbon atoms. More particularly, this invention relates to such oxidation which is carried out by reacting such compounds with an effective amount of sulfur in water at high temperatures and pressures.

SUMMARY OF THE INVENTION

The present invention is directed to a process for oxidizing organic compounds having allylic or benzylic carbon atoms. More particularly, the process of this invention comprises reacting an organic compound having one or more allylic or benzylic carbon atoms with an effective amount of an effective oxidizing agent in water at a temperature equal to or greater than about 350° C. and at a pressure equal to or greater than about 175 atmospheres, wherein said agent is selected from the group consisting of elemental sulfur, an oxidized form of elemental sulfur and, an organic or inorganic compound capable of forming elemental sulfur or said oxidized forms in situ under process conditions.

DESCRIPTION OF THE PREFERRED EMBODIMENTS

In the process of this invention, an organic compound having one or more allylic or benzylic carbon atoms is reacted with an effective amount of an oxidizing agent at a temperature equal to or greater than about 350° C., and at a pressure equal to or greater than 175 atmospheres. As used herein, an "organic compound having one or more allylic or benzylic carbon atoms" is an aliphatic, aromatic or heterocyclic compound having a carbon-atom bonded directly to a carbon-carbon double bond. As is apparent from the foregoing, such compounds may vary widely, the only requirement is that the compound include one or more structures of the formulas:

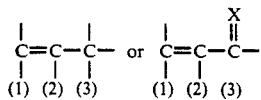

Where carbon atom number three (3) is the required benzylic or allylic carbon atom, and where X is a heteroatom such as oxygen, nitrogen, or sulfur. Illustrative of such compounds are arenes such as alkylbenzene and other mono and polysubstituted aromatics including toluene, xylenes, mesitylene, benzylchloride, o-chlorotoluene, p-chlorotoluene, ethylbenzene, benzal chloride, 2-bromo-1-phenylethane, benzylbromide, o-nitrotoluene, n-butylbenzene, 1,2,4,5-tetramethyl benzoic acid, 1-phenylethanol, 1-phenyl-2-chloropropane, 1-phenylpropene, 1-phenylpropanol, 3-phenylpropene,1-phenylethylene glycol, phenylacetylene, 1-acetamide-2-nitro naphthalene, 1-acetylnaphthalene, 2-acetyl-1-aminonaphthalene 1-amino-3-methylnaphthalene, 2-amino-6-methylnaphthalene, 1-(2-aminoethyl)-naphthalene, 2-benzyl-1-hydroxynaphthalene, 1,5-diamino-2-methylnaphthalene, 1,6-dimethyl-4-isopropylnaphthalene, 2,3-dimethylnaphthalene, 2-ethylnaphthalene, 1,2,7-trimethylnaphthalene, 10-methyl-1,2-benzanthracene, benzaldehyde, 2-methylbenzaldehyde, 9,10-dimethyl-1,2-benzanthracene, 3,4-dimethylbenzaldehyde, 3,3'-dimethyl-1,1-binaphthyl, 1,3,5-triacetylbenzene, 4,4'-dihydroxy-3,3'diethyl-5,5'-dimethylbiphenyl, benzophenone, 2,4,5-trimethylbenzoic acid, 2-(2-tolyyl)benzoic acid, 4,4'-dimethylbenzophenone, 2,3'dimethylbiphenyl, 4,4'-dimethylbiphenyl, 4-methylbenzophenone, 1,3-dimethylanthracene, 9-ethylanthracene, 2,3-dimethylanthracene, 2-methylanthracene, 9-acetyl-phenanthrene, 7-isopropyl-1-methylphenanthrene, 3-methylphenanthrene, 9-ethylphenanthrene, and the like.

Also illustrative of useful allylic and benzylic compounds are substituted heterocyclic compounds as for example, 5,6-dimethylbenzimidazole, 5-methylbenzimidazole, 2-methylbenzimidazole, 3-methylbenzisoxazole, 2-methylbenzofuran, 5-methyl-benzofuran, 7-methylbenzofuran, 2-methylbenzothiazole, 5-chloro-2-methylbenzothiazole, 2-methyl-2-iminobenzothiazolene, 2-methylbenzoxazole, and the like.

Exemplary of useful aliphatic allylic and benzylic compounds are propenes, isobutylene, 2,4,4-tri-methyl-2-pentene, 1-butene, 1-pentene, 1-heptene, 3-methyl-1-butene,2,3-dimethyl-1-butene, 2-methyl-1-2-butene, 2-butene, 2-methyl-2-butene, 3,3-dimethyl-butene, 4,4-dimethylpentene and the like.

Preferred for use in the practice of this invention are arenes in which the benzylic carbon is oxidized to form a carbon atom substituted with a hydroxy croup, or is converted into a carbonyl group or into a carboxyl group which may be decarboxylated under process conditions to form the unsubstituted arene. Particularly preferred for use in the practice of this invention are benzene substituted with one or more substituents at least one of which is an alkyl group. Other benzylic compounds which are particularly suited for use in the process of this invention are naturally occurring materials or process residues from such materials which comprise arenes having one or more alkyl substituents such as low grade coals such as lignite and bituminous cost, heavy crude oil, heavy hydrocarbon extracted from tar sands, commonly called tar sand bitumen, such at Athavasca tar sand bitumen obtained from Canada, heavy petroleum crude oils, such as Venezuelan Orinoco heavy oil belt crudes (Boscan heavy oil), heavy hydrocarbon fractions obtained from crude petroleum oils particularly heavy vacuum gas oils, vacuum residues, petroleum tars, coal tars and shale oils. These naturally occurring materials which may contain alkyl substituted arenes can be conveniently processed in accordance with this invention to produce carboxylic acid substituted arenes such as benzoic acid, 1-anthracene carboxylic acid, 1-naphthalene carboxylic acid or 1-phenathrene carboxylic acid, or can be reacted under conditions such that the corresponding decarboxylated arene such as benzene, anthracene or phenathrene is formed.

Effective oxidizing agents are selected from the group consisting of elemental sulfur, oxidized forms of elemental sulfur, and sulfur containing organic or inorganic compounds capable of forming elemental sulfur or such oxidized forms in situ under the process condition. Illustrative of useful oxidized forms of sulfur and such compounds are sulfur dioxide, and oxyacids of sulfur which generate sulfur dioxide on heating in water, such as sulfurous acid, and hydrosulfurous acid, and metal and non-metal salts thereof such as ammonium sulfite, ammonium bisulfite, sodium sulfite, sodium bisulfite, calcium sulfite, calcium bisulfite, and the like.

Also illustrative of effective oxidizing agents which form elemental sulfur, and oxidized forms thereof under process conditions are organo sulfur compounds as for example mercaptans, such ethylmercaptan, and methyl mercaptan; dialkylsulfites; dialkylsulfides, and the like.

Preferred for use in the practice of this invention as the oxidizing agent is elemental sulfur, sulfur dioxide, and sulfur containing inorganic acids such as sulfurous acid, hydrosulfurous acid, and their salts such as inorganic sulfites and bisulfites, preferably the ammonium, alkali metal and alkaline earth metal sulfites and bisulfites. Particularly preferred for use in the practice of this invention is elemental sulfur and sulfuric dioxides and bisulfite salts.

An "oxidizing effective amount" of one or more effective oxidizing agents is employed. As used herein, an "oxidizing effective amount" is an amount of such agents which is effective to oxidized the benzylic or allylic carbon atoms to the desired extent. In general, the amount of oxidizing agent employed is at least 0.9 equivalents based on the total equivalents of oxidizable benzylic and allylic carbon atoms contained in the organic compound. The upper limit for the oxidizing agent is not critical. In general, to obtain the desired stoichiometric oxidation of allylic and benzylic carbon atoms, the amount employed is at least about the stoichiometric amount required to form the desired oxidation product. In the preferred embodiments of the invention, the amount of oxidizing agent employed is from about 1.0 equivalent to about 3.0 equivalents based on the total equivalents of oxidizable allylic or benzylic carbon atoms contained in the organic compound to form the desired oxidation product, and in the particularly preferred embodiments, the amount of oxidizing agent employed is from about 1.5 to about 2.5 equivalents on the aforementioned basis. Amongst these particularly preferred embodiments, most preferred are those embodiments in which the amount of oxidizing agent is 200% of the stoichiometric amount required to oxidized the oxidizable allylic and benzylic carbon atoms contained in the organic compound to form the desired oxidation product.

The amount of water employed is not critical. In general, an amount is employed which is sufficient to dissolve the organic compound to some degree at the process temperature and pressures. In general, the amount of water is at least about ten times the total number of moles of the organic compound. While the upper amount of the water is not critical, in general, the amount employed is not less than about 5.0 times the total weight of the organic compound. In the preferred embodiments of the invention, the amount of water is from about seven to about nine times the total weight of the organic compound and the oxidizing agent.

Process temperatures and pressures are critical. In general, the process is carried out at a temperature equal to or greater than about 350° C. and a pressure equal to or greater than about 175 atmospheres. In the preferred embodiments of the invention, the process is carried out at a temperature equal to or greater than about 360° C. and a pressure equal to or greater than about 200 atmospheres, and in the particularly preferred embodiments of the invention, the process is carried out at supercritical conditions of water, i.e., temperatures equal to or greater than about 374° C. and pressure equal to or greater than about 218.3 atmospheres. Amongst these particularly preferred embodiments, most preferred are those embodiments in which process temperatures are about 400° C. and at a pressure of about 225 atmospheres.

The process is carried out for a time sufficient to oxidize the allylic or benzylic carbon atom to the desired extent. Residence times are not critical and can vary widely depending on such factors as the susceptibility of the benzylic or allylic carbon atoms to oxidation, the reaction temperature and pressure and the like. Usually residence times are in the range of from about 0.1 to about 5 hours. In the preferred embodiments of the invention residence times are from about 0.5 to about two hours, and in the particularly preferred embodiments residence times are in the range of from about 0.75 to about 1.25 hours.

The process of this invention can be conducted in batch, semicontinuous or continuous fashion. In the preferred embodiments of the invention, the process is carried out in a semi-continuous or continuous fashion, and in the particularly preferred embodiments of the invention, the reaction is carried out in a continuous fashion.

The reaction may be conducted in a single reaction zone or in a plurality of reaction zones, in series or in parallel or it may be conducted intermittently or continuously in an elongated tubular zone or series of such zones. The materials of construction employed should be inert to the reactants during the reaction and the fabrication of the equipment should be able to withstand the reaction temperatures and pressure.

The reaction zone can be fitted with one or more internal and/or external heaters in order to control undue temperature fluctuations, or to prevent any possible "runaway" reaction temperatures. In preferred embodiments of the process, agitation means to vary the degree of mixing the reaction mixture can be employed. Mixing by vibration, shaking, stirring, rotation, oscillation, ultrasonic vibration or the like are all illustrative of the type of agitation means contemplated. Such means are available and well known to those skilled in the art.

The reactants and reagents may be initially introduced into the reaction zone simultaneously or stepwise or it may be continuously or intermittently introduced in such zone during the course of the process. Means to introduce and/or adjust the quantity of reactants introduced, either intermittently or continuously into the reaction zone during the course of the reaction can be conveniently utilized in the process especially to maintain the desired molar ratio of the reaction solvent, reactants and reagents.

The oxidized products formed by the process of this invention can be recovered using standard recovery techniques and accordingly will not be described in great detail. Illustrative of useful recovery techniques are distillation, absorption, absorption and extraction. Such procedures are described in detail in Perry's Chemical Engineering Handbook published by McGraw-Hill, Inc., which is incorporated herein by reference.

Oxidized products produced by the process of this invention have many uses. For example, materials such as benzaldehyde, toluene, xylene, ethylbenzene, and heavy hydrocarbons such as heavy crude oil, heavy hydrocarbons extracted from tar sands commonly called tar sand bitumen, such as Athabasca tar sand bitumen obtained from Canada, heavy petroleum crude oils, such as Venezuelan Orinoco heavy oil belt crudes (Boscan heavy oil), heavy hydrocarbon fractions obtained from crude petroleum oils particularly heavy vacuum gas oils, vacuum residue as well as petroleum tar and coal tar or even shale oil can be reacted in the process of this invention with a suitable oxidizing agent such as elemental sulfur, or sulfur dioxide to form benzene, a useful industrial solvent, as well as other polynuclear aromatics.

The following examples are present to better illustrate the invention and should not be construed as limitation thereon.

EXAMPLE 1

Reactions were carried out in stainless steel microreactors made of Swagelop capped ends (¼" diameter). Ten mmols of nonadecane was weighed and reacted with 1.35g (75 mmols) of water. The microreactor was placed in Wood's Alloy bath heated by electric tapes. The temperature was controlled accurately to ± 2° using a Datatrak system. The heating was usually carried out for one hour. The microreactor was cooled in cold water and the contents extracted with CCl$_4$ (or other suitable organic solvents). The organic layer was dried and concentrated. The water layer was also concentrated to see if there were any products dissolved in it. Analysis using capillary column electron impact and chemical ionization gc/mass spectrometry, 'HNMR and it showed that nonadecane did not react and was recovered quantitatively.

EXAMPLES 2-10

The experiment described in Example 1 was repeated for the following hydrocarbons: n-octane, cis-decalin, trans-decalin, benzene, bibenzyl, naphthalene, toluene, ethylbenzene and diphenylmethane. Heating was carried out at 400° C. for one hour. Product analysis showed that none of the above compounds reacted.

EXAMPLES 11-26

The experiment described in Example 1 was repeated for 1-octene, 2-octene(cis-trans mixture), styrene, stilbene, 2-octanol, 1-phenylethanol, phenol, o-cresol, m-cresol, p-cresol, anisole, dibutylether, benzophenone, acetophenone, 2-octanone and deoxybenzoin. Heating was carried out at 400° C. for one hour. Product analysis showed that the above compounds did not react and were recovered quantitatively.

EXAMPLES 27 AND 28

The experiment described in Example 1 was repeated for phenylacetic acid, 3-thipheneactic acid and benzoic acid. Heating was carried out at 400° C. for one hour. The products were recovered and analyzed. Phenylacetic acid was converted entirely to toluene and 3-thiopheneacetic acid was converted to 3-methylthiophene in more than 90% yield. Benzoic acid was converted to an extent of 1-2% to benzene.

EXAMPLE 29

The experiment described in Example 1 was repeated for dibenzyldisulphide. Heating was carried out at 400° C. for one hour. Analysis showed that the compound has reacted completely to form toluene (41%), benzoic acid(29%), benzene(14%), bibenzyl(6%), deoxybenzoin(4%), 5-phenylbenzothiophene(5%) and anti-bibenzothiophene(1%).

when heated at 300° C. in water for one hour, the predominent products were toluene and bibenzyl. Benzoic acid and deoxybenzoin were formed in trace amounts. AT 250° C. (for 1 hour), the products were toluene(58%) and bibenzyl(42%). At 200° C., the only product observed was dibenzylsulphide.

EXAMPLE 30

The experiment described in Example 29 was repeated for dibenzylsulfide at 400° C. for one hour. The same product (except benzothiphenes) were obtained in slightly different ratios.

If the reaction was carried out in isopropanol (instead of water) at 400° C. for one hours, toluene(70%) and bibenzyl(30%) were the only products. If the reaction was run in methanol, toluene and bibenzyl were obtained in 25% and 75% yields respectively.

EXAMPLE 31

The experiment described in Example 30 was repeated for dibenzylsulfoxide in methanol medium for one hour at 400° C. An oxidation product (methylbenzoate) was observed in 20% yield in addition to toluene and bibenzyl which were formed to any extent of 30% and 50%, respectively. Elemental sulfur was also observed in the product and sulfur dioxide and hydrogen sulfide were detected in the gas phase and the liquid phase.

EXAMPLES 32-41

The experiment described in Example 1 was repeated for bibenzyl, deoxybenzoin and toluene with sulfur (3 molar excess) and water (or water saturated with sulfur dioxide at various temperatures). The results are tabulated in Table I.

In Table I, the abbreviations shall have the following meanings.
a. "T" = Toluene
b. "BA" = Benzoic Acid
c. "B" = Benzene
d. "BB" = Bibenzyl
e. "DOB" = deoxybenzoin
f. "BT" = Benzothiphenes

| Ex. No. | Reactant | Reagent | Temperature |
|---|---|---|---|
| Ex. 32 | BB | S° | 400° C. |
| Ex. 33 | DOB | S° | 400° C. |
| Ex. 34 | T | S° | 400° C. |
| Ex. 35 | T | S° | 350° C. |
| Ex. 36 | T | S° | 300° C. |
| Ex. 37 | T | S° | 250° C. |
| Ex. 38 | T | SO$_2$ | 400° C. |
| Ex. 39 | T | SO$_2$ | 350° C. |
| Ex. 40 | T | SO$_2$ | 300° C. |
| Ex. 41 | T | SO$_2$ | 250° C. |

| | Products (Mole %) | | | | | |
|---|---|---|---|---|---|---|
| Ex. No. | T | BA | B | BB | DOB | BT |
| Ex. 32 | 44 | 33 | 22 | 1 | 0 | 0 |
| Ex. 33 | 10 | 10 | 20 | 2 | 38 | 17 |
| Ex. 34 | 55.5 | 30.5 | 14.0 | Trace | 0 | 0 |
| Ex. 35 | 61.4 | 27.2 | 10.0 | 1.4 | 0 | 0 |
| Ex. 36 | 77.0 | 23.0 | 0 | 0 | 0 | 0 |
| Ex. 37 | 100 | 0 | 0 | 0 | 0 | 0 |
| Ex. 38 | 39.4 | 42.4 | 15.1 | 3.0 | 0 | 0 |
| Ex. 39 | 35.3 | 58.4 | 5.0 | 1.2 | Trace | 0 |
| Ex. 40 | 56.3 | 36.7 | 3.0 | 4.0 | Trace | 0 |
| Ex. 41 | 100 | 0 | 0 | 0 | 0 | 0 |

EXAMPLES 42-45

The experiment described in Example 1 was repeated for benzylmercaptan at various temperatures for one hour and the results tabulated in Table II.

IN Table II, the abbreviations have the following meanings:
a. "T" = Toluene
b. "BA" = Benzoic Acid
c. "B" = Benzene
d. "BB" = Bibenzyl
e. "DOB" = deoxybenzoin
f. "BT" = Benzothiphenes
g. "BM" = Benzylmercaptan

TABLE II

| Ex. No. | Reactant | Reagent | Temperature |
|---------|----------|---------|-------------|
| Ex. 42  | BM       | none    | 400° C.     |
| Ex. 43  | BM       | none    | 350° C.     |
| Ex. 44  | BM       | none    | 250° C.     |
| Ex. 45  | BM       | none    | 200° C.     |

| | Products (Mole %) | | | | | |
|---|---|---|---|---|---|---|
| Ex. No. | T | BA | B | BB | DOB | BT |
| Ex. 42 | 54.5 | 31.8 | 6.8 | 3.4 | 3.4 | 0 |
| Ex. 43 | 61.5 | 30.8 | 2.0 | 3.0 | 2.7 | 0 |
| Ex. 44 | 71.7 | Trace | 0 | 17.9 | 10.2 | 0 |
| Ex. 45 | 0 | 0 | 0 | 0 | 0 | 0 |

EXAMPLE 46

When diphenylmethane or benzophenone were heated with one molar ratio of sulfur in water at 400° C. for one hour as described in Example 1, the same equilibrium mixture of diphenylmethane (35%) and benzophenone (65%) was obtained.

EXAMPLE 47

When diphenylmethane was heated in water (containing one mole ratio of sodium bisulfite) at 400° C. for one hour as described in Example 1, it was converted quantitatively to benzophenone.

EXAMPLE 48

When heated with one mole equivalent of sulfur in water at 400° C. as described in Example 1, ethylbenzene is converted to acetophenone, toluene, benzoic acid and benzene.

EXAMPLE 49

When acetophenone was heated with one mole equivalent of sulfur in water at 400° C. for one hour (as described in Example 1), it was converted to a product mixture almost identical to the one obtained in Example 48.

What is claimed is:

1. A process for oxidizing benzylic and allylic carbon atoms which comprises reacting an organic compound having one or more benzylic carbon atoms, allylic carbon atoms or combinations thereof with an oxidizing effective amount of an effective oxidizing agent in water at a temperature equal to or greater than about 350° C. and at a pressure equal to or greater than about 175 atmospheres, to oxidized said benzylic carbon atoms, allylic carbon atoms or combinations thereof, said effective oxidizing agent selected from the group consisting of sulfur containing oxy acids which form sulfur dioxide under process conditions and salts thereof.

2. A process of claim 1 wherein said process is carried out at a temperature equal to or greater than about 360° C. and a pressure equal to or greater than about 200 atmosphere.

3. A process according to claim 1 wherein said process is carried out at a temperature and pressure equal to or greater than the critical temperature and pressure of water.

4. A process according to claim 3 wherein said temperature is equal to about 400° C.

5. A process according to claim 1 wherein said acids are selected from the group consisting of sulfurous acid, hydrosulfurous acid, and the salts thereof.

6. A process according to claim 5 wherein said agent is selected from the group consisting of the alkaline earth metal, alkali metal and ammonium salts of said acids.

7. A process according to claim 5 wherein said agent is selected from the group consisting of bisulfite salts.

8. A process according to claim 1 wherein said organic compounds are selected from the group consisting of substituted arenes wherein at least one of the substituents is an alkyl group.

9. A process according to claim 8 wherein said arenes are selected from the group consisting of alkyl substituted benzene, anthracene, phenanthrene, and naphthalene.

10. A process according to claim 9 wherein said arenes are selected from the group consisting of alkyl substituted benzene.

11. A process according to claim 1 wherein said organic compounds comprise heavy hydrocarbons.

12. A process according to claim 11 wherein said heavy hydrocarbons are selected from the group consisting of low grade coals, heavy crude oil, heavy hydrocarbons extracted from tar sands, heavy petroleum crude oils, shale oil, and heavy hydrocarbon fractions obtained form crude petroleum oils.

13. A process according to claim 1 wherein the amount of said oxidizing agent is at least about 0.9 equivalents based on the total equivalents of allylic and benzylic carbon atoms.

14. A process according to claim 13 wherein said amount is from about 1.0 to about 5.0 equivalent %.

15. A process according to claim 13 wherein said amount is from about 2.0 to about 4.0 equivalent %.

16. A process according to claim 1 wherein an excess of said oxidizing agent is used.

17. A process according to claim 7 wherein said effective oxidizing agent is an alkali metal bisulfite.

18. A process according to claim 17 wherein said alkali metal bisulfite is sodium bisulfite.

19. A process according to claim 1 wherein said organic compound is an arylmethylenearyl compound.

20. A process according to claim 19 wherein said arylmethylenearyl compound is diphenylmethane.

21. A process according to claim 19 wherein said agent is an alkali metal bisulfite.

22. A process according to claim 21 wherein said agent is sodium bisulfite.

23. A process according to claim 20 wherein said agent is an alkali metal bisulfite.

24. A process according to claim 23 wherein said alkali metal bisulfite is sodium bisulfite.

* * * * *